United States Patent
Amberg et al.

(10) Patent No.: US 9,872,655 B2
(45) Date of Patent: *Jan. 23, 2018

(54) PAE TREATMENT FOR BPH

(75) Inventors: Jessica Amberg, Bubenreuth (DE); Hayo Knoop, Forchheim (DE); Stefan Lautenschläger, Hausen (DE); Kerstin Sonntag, Fürth (DE)

(73) Assignee: Siemens Aktiengesellschaft, München (DE)

( * ) Notice: Subject to any disclaimer, the term of this patent is extended or adjusted under 35 U.S.C. 154(b) by 169 days.

This patent is subject to a terminal disclaimer.

(21) Appl. No.: 13/435,583

(22) Filed: Mar. 30, 2012

(65) Prior Publication Data

US 2013/0261431 A1 Oct. 3, 2013

(51) Int. Cl.
G06K 9/00 (2006.01)
A61B 6/12 (2006.01)
A61B 6/03 (2006.01)
A61B 6/00 (2006.01)

(52) U.S. Cl.
CPC ............... *A61B 6/12* (2013.01); *A61B 6/487* (2013.01); *A61B 6/504* (2013.01); *A61B 6/5235* (2013.01); *A61B 6/032* (2013.01); *A61B 6/4441* (2013.01); *A61B 6/507* (2013.01)

(58) Field of Classification Search
CPC ......... G06T 2207/30101; G06T 7/0012; G06T 2207/10068; G06T 2207/30096; G06T 2207/10024; A61B 5/0075; A61B 5/0084; A61B 17/12022; A61B 5/7264; A61B 5/4331; A61B 6/12; A61B 6/487; A61B 6/504; A61B 6/5235; A61B 6/032; A61B 6/4441; A61B 6/507; G06F 19/3431; G06K 9/6282

USPC ....................................... 382/128; 378/4, 62
See application file for complete search history.

(56) References Cited

U.S. PATENT DOCUMENTS

| | | | |
|---|---|---|---|
| 2006/0257031 A1* | 11/2006 | Abramoff et al. ............ 382/224 |
| 2007/0208250 A1* | 9/2007 | Sullivan ................. A61B 5/064 600/410 |
| 2008/0208052 A1* | 8/2008 | LePivert ................ A61B 18/02 600/439 |
| 2008/0275467 A1* | 11/2008 | Liao et al. ..................... 606/130 |
| 2010/0092064 A1* | 4/2010 | Li ................................ 382/133 |
| 2011/0282193 A1 | 11/2011 | Amberg et al. |

OTHER PUBLICATIONS

Product literature, "*syngo* Embolization Guidance—Enhanced Planning and Guidance," Siemens AG (Nov. 2010).

* cited by examiner

*Primary Examiner* — Elmer Chao

(74) *Attorney, Agent, or Firm* — Lempia Summerfield Katz LLC

(57) ABSTRACT

A method of guiding a catheter during an embolization operation includes receiving volume data of a patient volume, the patient volume including a lesion and a feeding vessel for the lesion, detecting the feeding vessel in the volume data, define a vessel connection path for the feeding vessel, the vessel connection path connecting first and second points in the volume data, the second point being disposed along the feeding vessel, receiving fluoroscopic projection data of the patient volume, and rendering the fluoroscopic projection data with an overlay during the embolization operation, the overlay including the vessel connection path for the feeding vessel.

24 Claims, 3 Drawing Sheets

PAE TREATMENT FOR BPH

BACKGROUND

The present embodiments relate to imaging-based medical procedures.

Symptomatic benign prostatic hyperplasia (BPH) is common among older men. In BPH, an enlarged prostate gland presses on the urethra, constricting the flow of urine. Over 40% of men above the age of 60 experience a host of uncomfortable symptoms due to a BPH tumor or lesion, including hesitancy, decreased urinary stream, intermittency, sensation of incomplete emptying, nocturia, frequency, and urgency.

Management of BPH varies based on the overall health of the patient and the severity of the symptoms. Various medications can decrease the severity of the voiding symptoms. Minimally invasive techniques have been developed for treatment of BPH. Examples include transurethral microwave thermotherapy and other laser ablations. Prostatectomy via transurethral or open surgical techniques is the traditional surgical treatment. Such surgical intervention is considered to be high risk given the advanced age of the typical patient.

Prostate artery embolization (PAE) has been used to control hemorrhaging after prostatectomy or prostate biopsy operations. PAE delivers particles to a blood vessel to block flow. A recent experimental study of PAE in pigs showed a reduction in prostate volume after embolization to block blood flow to the lesion.

Imaging of blood vessels supplying a lesion is used to help a physician guide a catheter to a position for a vascular intervention procedure. Two-dimensional (2D) X-ray fluoroscopy is routinely used for vascular interventions. Fluoroscopy is used for real-time monitoring of the procedure and catheter location visualization. The vessels of interest in fluoroscopy are opacified by injecting contrast agent into the patient. Preoperative three-dimensional (3D) imaging data from computed tomography (CT) or magnetic resonance imaging (MRI) systems are used to provide a high-quality visualization of the body anatomy.

The vasculature supplying a BPH lesion may be complex. It may be difficult for the physician to guide the catheter despite the assistance of the fluoroscopic and other imaging data provided during the procedure.

BRIEF SUMMARY

By way of introduction, the preferred embodiments described below include methods, systems, instructions, and computer readable media for supporting an embolization procedure via a display or rendering of one or more vessel connection paths defined for one or more feeding vessels for a lesion. In one embodiment, volume data of a patient volume is used to detect the feeding vessel(s) and to define points to be connected by the vessel connection path(s).

In a first aspect, a method is provided for guiding a catheter during an embolization operation for a lesion. The method includes receiving volume data of a patient volume, the patient volume including the lesion and a feeding vessel for the lesion, detecting the feeding vessel in the volume data, defining a vessel connection path for the feeding vessel, the vessel connection path connecting first and second points in the volume data, the second point being disposed along the feeding vessel, receiving fluoroscopic projection data of the patient volume, and rendering the fluoroscopic projection data with an overlay during the embolization operation, the overlay including the vessel connection path for the feeding vessel.

In a second aspect, a non-transitory computer readable storage medium has stored therein data representing instructions executable by a programmed processor for guiding a catheter during an embolization operation for a lesion. The instructions include computer code to receive volume data of a patient volume, the patient volume including the lesion and a feeding vessel for the lesion, detect the feeding vessel in the volume data, define a vessel connection path for the feeding vessel, the vessel connection path connecting first and second points in the volume data, the first point being disposed along an artery for the feeding vessel and the second point being disposed along the feeding vessel, and render an image from fluoroscopic projection data during the embolization operation, the image additionally including the vessel connection path for the feeding vessel.

In a third aspect, a system is provided for guiding a catheter during an embolization operation for a lesion. The system includes a memory in which volume data of a patient volume is stored, an x-ray imaging system operable to generate fluoroscopic projection data for the patient volume, a processor configured to define a vessel connection path for a feeding vessel for the lesion and to render a representation of the fluoroscopic projection data with the vessel connection path, and a display operable to display the representation during the embolization operation. The processor is further configured to detect the feeding vessel in the volume data, the vessel connection path connecting first and second points in the volume data, the first point being disposed along an artery for the feeding vessel and the second point being disposed along the feeding vessel.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
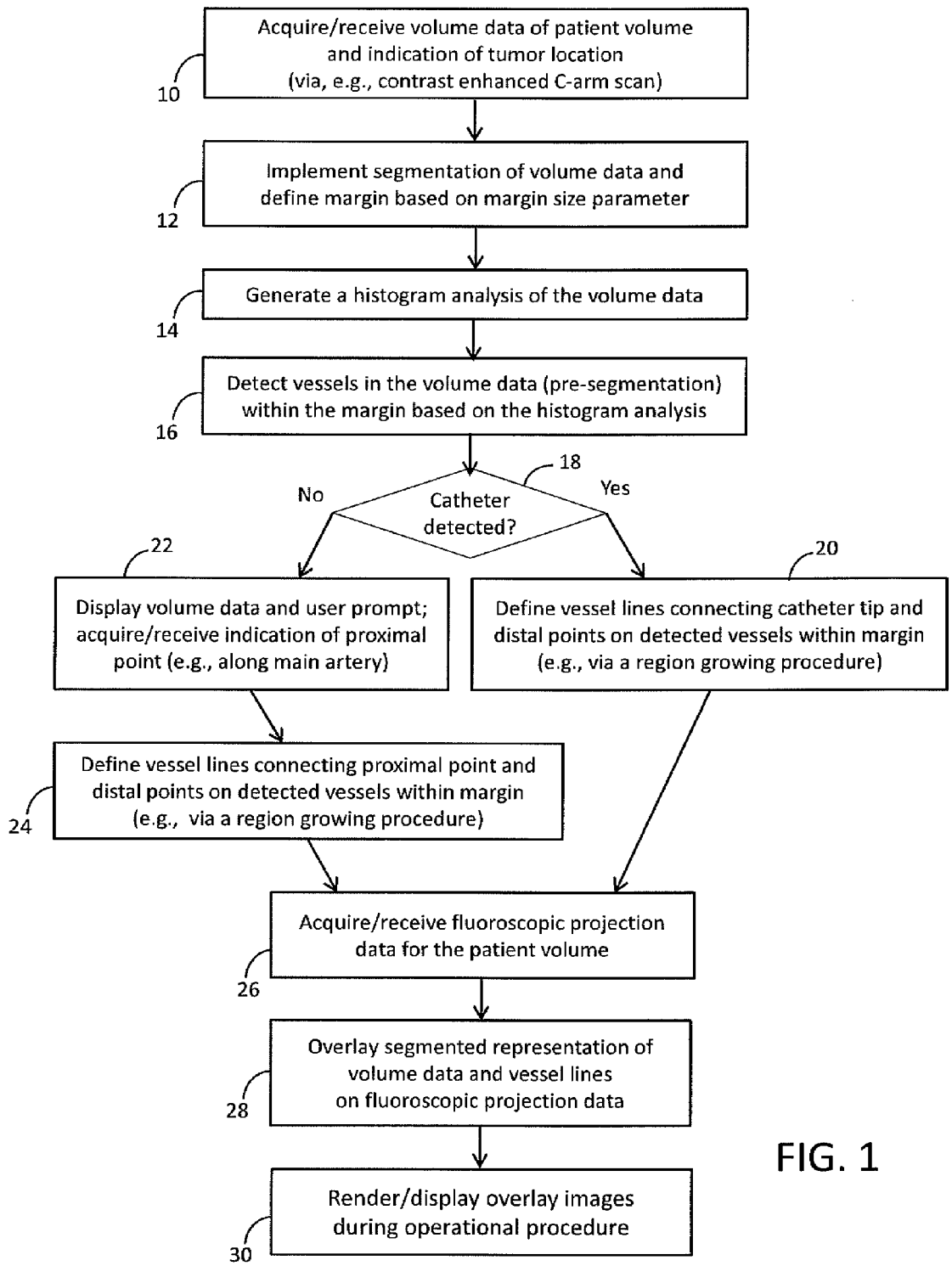
FIG. 1 is a flow chart diagram of one embodiment of a method for displaying a catheter position relative to a patient volume during an embolization operation.

Systems, methods, and computer readable media are provided to support an embolization operation, including, for instance, an embolization intervention directed to treating BPH. Volume data is used to enhance a 2D display (e.g., projection) of fluoroscopic data captured during the embolization operation. The volume data is used to overlay vessel connection paths or lines and a segmented representation of a prostate lesion or tumor on a display or other rendering of the fluoroscopic data.

The disclosed methods may in some cases allow imaging, planning, and/or intervention procedures to be implemented in a single, common site, e.g., an angiography site. The patient may thus no longer need to be transported from a radiology or other location to implement the embolization operation. The cost of the embolization operation may be reduced for these and other reasons.

The operation may be completed more quickly due to the real-time rendering of the fluoroscopic data with the vessel path overlay. Presentation of the overlay information (including the segmented representation of the lesion) during the intervention provides a clear indication of the correct path for the catheter. The decrease in time may, in turn, decrease the amount of contrast agent and X-ray dose for the operation. For example, the time under fluoroscopy and the number of digital subtraction angiography (DSA) acquisitions may be reduced.

The automation of the disclosed methods may simplify the clinical workflow for the physician. The decrease in user interaction may increase the likelihood of success and enable more physicians, or types of physicians (e.g., urologists) to perform the operation. Reliance on the disclosed methods may not involve extensive familiarity with the radiological systems.

In one embodiment, a contrast-enhanced 3D volumetric dataset of a patient volume is acquired. The dataset may be obtained via a rotational CT scanner, a CT system, an MR system, or other imaging system. The intra-artery injection of contrast agent may be used to enhance the representation of the vessels feeding the lesion.

Implementation of the disclosed methods may be automated to a significant extent. Input from a physician or other operator may be limited to marking or otherwise identifying or indicating a lesion in the 3D dataset. A single marker may be used in some cases.

After the system receives the indication of the location of the lesion, a segmentation procedure is implemented to further identify the lesion in the 3D dataset. A volumetric measurement of the patient volume based on the lesion segmentation may then be presented. For example, volumetric measurement data may be presented by rendering the corresponding structures with a dedicated color (e.g., red) and/or providing a volumetric value (e.g., segmentation=10.7 milliliters).

A margin around the segmented lesion may be created or defined. The lesion margin may have a predetermined size. The margin size may be an adjustable parameter.

The 3D dataset may be analyzed to identify the contrast-enhanced vessels feeding the lesion. The analysis may include a histogram analysis. The vessels may be identified via a pre-segmentation procedure based on the histogram or other analysis. A position or point on each vessel within the lesion margin may then be detected.

If the 3D dataset is generated during the embolization operation, e.g., by a rotational CT scanner (e.g., DynaCT), a catheter may be positioned within the patient volume. A tip of the catheter may then be detected automatically, and used as one of two points along a vessel connection path to guide the physician during the embolization operation. The position of the catheter tip is connected with a respective position on each vessel, which serves as the second point. The position on the vessel may be within a lesion margin. The vessel connection path or line is thus defined with respect to the volume data. The previously detected, pre-segmentation vessels may be used as guides to define the vessel connection path between the points. Region-growing and other procedures may be implemented to define the connecting vessel connection paths.

In some embodiments, the catheter tip is not present in the 3D dataset (e.g., CT, MRI, or other preoperative 3D datasets, and/or when the patient volume is too small to capture the catheter tip). The physician may then be prompted to mark or otherwise identify a primary or main artery supplying the plurality of vessels for the lesion. The marking or identification of the primary artery provides one of the points for definition of the vessel connection path. The point along the primary artery may then be connected with the feeding vessels until reaching the point within the lesion margin.

The disclosed methods may be used with a wide variety of scanners or imaging systems to generate pre-operative volume data. In embodiments relying on CT, MRI, or other preoperative 3D datasets, a rotational CT scan (e.g., a low dose DynaCT scan) may be implemented to acquire volume data during the embolization operation. The preoperative 3D dataset may then be fused with such volume data to transform or register the preoperative 3D dataset to the coordinate system of the imaging system used during the embolization procedure. The nature of the transformation or registration may vary to accommodate the differences between the pre-operative and intraoperative datasets.

Although described in connection with BPH treatment procedures, the methods, systems, and computer readable media are not limited to the context of treatment procedures addressing BPH. The methods, systems, and computer readable media are well suited for application in a variety of tumor treatment procedures in which a catheter or other medical instrument is displayed relative to an anatomical volume during the procedure. The treatment procedures need not be considered minimally invasive, and may thus involve invasive elements or include invasive procedures, including, for instance, surgical procedures. The methods, systems, and computer readable media may be applied to improve the display of a wide variety of anatomical structures other than the prostate gland.

FIG. 1 depicts a method of guiding a catheter during an embolization operation for a lesion, such as a tumor leading to BPH. The method may begin with acquiring or receiving in act 10 volume data of a patient volume. The patient volume includes the lesion or any portion thereof, as well as a plurality of feeding vessels for the lesion. In BPH embodiments, the patient volume includes the prostate gland and surrounding vasculature. In one embodiment, the volume data may be acquired via one or more computer tomography (CT) imaging or scanning sequences or procedures. Such procedures may be implemented using x-ray or other radiography equipment. Alternatively or additionally, the volume data is obtained via other imaging modalities, such as positron emission tomography (PET), single photon emission computed tomography (SPECT), and/or 3D magnetic resonance imaging (MRI). The preliminary volume data may be obtained via any one or more imaging modalities. Contrast agent may be injected into an artery in or near the patient volume to facilitate the acquisition of volume data indicative of the blood vessels feeding the lesion.

The volume data may be preliminary or pre-operative volume data. The imaging or scanning that leads to the preliminary volume data may be implemented before the catheter-based embolization procedure. The catheter and other medical equipment involved in the embolization procedure may not be present in the patient. The imaging or scanning may be implemented for purposes other than supporting or facilitating the embolization procedure. For example, the imaging or scanning may be implemented to assess the size of the lesion. The assessment may be useful in diagnosing the severity of the BPH condition. For example, the CT or MRI data is acquired prior to the embolization procedure, such as just prior to (same day) or during a previous appointment on a different day. The data represents tissue, and may be in a high resolution.

The preliminary volume data may alternatively be obtained solely for the purpose of supporting the embolization procedure. The imaging or scanning that generates the preliminary volume data may thus be implemented commensurate or otherwise in connection with the embolization procedure.

After the acquisition or reception of the preliminary volume data, such as CT volume data, the volume data may be stored in a memory or other data store. The preliminary volume data may be stored in a database, a file, or any other data structure. The data storage need not be non-volatile, and may instead involve a volatile memory accessed during implementation of the embolization procedure and the disclosed methods.

The preliminary volume data may be computed using any image reconstruction or CT data processing technique. For example, the CT volume data may be generated from any number of x-ray projections or other 2D scans. In one embodiment, the preliminary volume data is generated by a rotational C-arm X-ray imaging system, such as the DynaCT imaging system commercially available from Siemens Healthcare.

In act 12, the volume data is processed to locate the BPH lesion or tumor and thereby define a representation of the lesion in the volume data. The processing may include the implementation of a segmentation procedure. Any image segmentation procedure may be used. For example, the procedure may include one or more of a clustering method (e.g., k-means clustering), a compression-based method, a histogram analysis, edge detection procedure, and/or a region-growing method. Additional, fewer, or alternative methods may be implemented.

The processing of the volume data to locate the lesion may include a user prompt to place one or more markers on a display of the volume data. The volume data may accordingly be rendered or otherwise processed to support the marking or other annotation of the volume data. Implementation of the segmentation procedure may then proceed based on the marking(s).

In some cases, one or more of the segmentation methods and procedures may be implemented to support other acts of the method directed to detecting the feeding vessels supplying blood to the lesion. Certain aspects of act 12 may thus be shared with other acts of the method. For instance, a histogram analysis of the volume data may be implemented in act 14. The histogram analysis may be directed to detecting the feeding vessels. The analysis is accordingly not limited to the volume data indicative of the lesion. In one example, the histogram analysis may include an analysis of the entire dataset for the patient volume (e.g., the pre-segmentation volume data) to determine an average gray value (e.g., 850 in a normalized range from 0-1000, with 1000 being black) and a search for voxels in the pre-segmentation dataset with a gray value exceeding a value based on the average gray value (e.g., 750). Voxels with higher gray values have a high probability of being part of a vessel because of the contrast agent. In alternative cases, only the volume data associated with locations outside of the lesion is analyzed to detect the feeding vessels.

The feeding vessels in the volume data are then detected. Detecting the feeding vessels may include determining which vessels are feeding the lesion. The determination need not involve detecting the vessels within a margin of the lesion. For instance, the vessels feeding the lesion may be identifiable in some cases. In other cases, it may be helpful to detect the vessels (e.g., feeding vessels) within a margin of the lesion. The margin may be determined based on the boundary and/or size of the lesion known from the results of the segmentation procedure. One or more predetermined margin size parameters may be used to determine the margin boundary. The parameter(s) may determine the margin in a relative or fixed manner. In some embodiments, the margin is determined based on the boundary and diameter of the lesion. For example, the margin is determined by extending the boundary outward by an amount corresponding with 10% of the lesion diameter. The extension outward may be computed for each point along the boundary of the lesion. The parameter may be based on characteristics of the lesion other than the diameter. Other examples may add a fixed distance to each point along the boundary. Still other examples may involve determining the margin size via a hybrid approach in which the lesion diameter is used as one parameter and another parameter is determinative of a minimum margin distance from the lesion boundary. Once the margin around the lesion is known, a point or other location in the volume data representative of each feeding vessel within the margin may be identified based on the histogram analysis.

The volume data may be further analyzed in connection with a decision block 18 directed to determining whether the catheter can be detected in the patient volume. For instance, the catheter tip may be positioned within the patient volume if the volume data is acquired by, e.g., a C-arm x-ray scan, during the embolization intervention. In some cases, the catheter tip may not be positioned within the patient volume due to the limited size of the patient volume. In other cases, the catheter tip is not present because the volume data is preliminary or preoperative data acquired before the intervention.

The analysis of the volume data to detect the catheter tip may include any one or more image processing techniques or procedures. The processing to detect the catheter tip may be initiated and implemented automatically. The processing may be implemented before, during, or after the histogram analysis, image segmentation, and other processing of the volume data.

If the catheter tip is detected within the volume data, then control passes to act 20, in which vessel lines or connection paths are defined connecting the catheter tip with the feeding vessels detected within the lesion margin. The catheter tip may constitute a proximal point on each vessel connection path. The point on each feeding vessel within the lesion margin may constitute a distal point on each vessel connection path. The path between the proximal and distal points may be determined via one or more image processing techniques or procedures. For instance, the results of the histogram analysis may be used as guide data to determine the connection path between the proximal and distal points. In one example, a region-growing procedure is implemented on the volume data. Additional or alternative procedures may be implemented. The data found to be indicative of the feeding vessels may be used in a manner similar to a map of the volume data providing or suggesting one or more potential routes.

The catheter tip may be located within a primary artery for the feeding vessels when the definition of the connection paths is initiated. The disclosed methods may include the generation of a user prompt to ask the user when to begin definition of the vessel connection paths. The physician may thus rely on a real-time rendering of the patient volume to determine when the catheter tip is disposed in a suitable location in the artery. Alternatively, the definition of the connection paths may be initiated automatically, e.g., upon detection of the catheter tip.

These and other acts of the disclosed method may be repeated for one or more feeding vessels associated with a different artery. Implementation of the method may thus allow the physician to define different proximal or starting points for different feeding vessels. A vessel connection path may be defined in act 20 for each feeding vessel detected in act 16 to eliminate, or maximize the reduction in, blood flow to the lesion.

The method also allows a vessel connection path for each feeding vessel to be defined when the catheter tip is not detected in the volume data. The catheter tip may not be present due to the preoperative nature of the volume data, or due to the size or location of the patient volume. In such cases, control passes to act 22, in which a representation of the volume data is displayed to support a user selection of the proximal point for the path. The selection may include the placement of a marker or other indicator on a rendering of the volume data. The act 22 accordingly includes receipt of a user specification of a position or location indicative of the point along the artery for the feeding vessels. The location of the indicator may then be used to determine the location of the proximal point in the volume data. The point may be disposed along an artery for all or any number of the feeding vessels. In some cases, the artery is a primary artery for the prostate gland, such as the Aorta iliac communis or the Aorta iliac interna. The location of the point along the artery may vary.

The respective vessel connection paths connecting the user-specified proximal point along the artery and the distal points within the margin are then defined in act 24 along each respective feeding vessel. Each connection path may be defined as described above, using the detected feeding vessels as guides between the proximal and distal points. A region-growing or other procedure may be implemented.

Each vessel connection path may be used by the physician for guidance purposes during the embolization procedure. In the example shown in FIG. 1, the volume data is acquired during the intervention, such that the same scanner used to generate the volume data is also being used to generate a real-time projection of the patient volume. For example, fluoroscopic projection data is acquired or received in act 26 for the patient volume. Such projection data may be acquired via a rotational X-ray scanner with a fluoroscopy display system, such as the above-referenced DynaCT system.

In act 28, a representation of the vessel connection paths is overlaid on the projection data. The overlay may include a line that tracks the connection path as the path runs from the proximal point to the distal point. The overlay may also include the segmented representation of the volume data. In this example, overlay images of the vessel connection paths and the lesion are generated in act 30 for display with the projection data during the intervention. The manner in which the overlay is generated may vary. In some embodiments, the syngo iPilot data processing system commercially available from Siemens Healthcare is used. The volume is rendered by projection to a viewing plane or based on a viewing direction the same as the projection of the fluoroscopy data. Other systems or procedures for rendering a visualization of the volume data, the fluoroscopic projection data, and the overlay data may be used.

The overlay may allow the real-time images to be generated and displayed for guidance purposes during the intervention without the use of contrast agent. Limiting the number of repeated injections of contrast agent may be beneficial for the patient. In embodiments or situations where contrast is still useful or desired, the overlay may allow the total amount of contrast agent to be reduced or minimized.

The number of proximal points defined during implementation of the disclosed methods may vary. A recursive loop may be included to address those situations in which a vessel connection path has yet to be defined for one or more feeding vessels detected in act 16. The number of distal points may also vary based on the number of feeding vessels detected, or as otherwise desired by the physician. One or more acts may be repeated until a desired number of vessel connection paths are defined and used.

Alternatively or additionally, another recursive loop may be included to determine whether blood flow to the lesion has decreased or been eliminated as a result of the embolization. The success of the embolization may be confirmed or checked via one or more image acquisition procedures. For example, further volume data may be obtained to confirm that the size of the lesion has decreased due to the loss of blood flow. The volume data may be processed as described above to identify the lesion. Such processing may include, for instance, image segmentation and other techniques. The timing of the image acquisition may vary from immediately after the intervention to one or more days after the intervention. The recursive loop may involve the repetition of one or more acts (or sets of acts) until a certain degree of success is achieved.

The efficacy of the embolization may alternatively or additionally be confirmed via one or more color Doppler flow scans of the lesion and surrounding volume. The color Doppler flow data may be obtained via ultrasound equipment located within or apart from the angiography suite. Such data may be obtained both before and after the intervention to support a comparative or other analysis of the blood flow to the lesion.

Figure 2A:
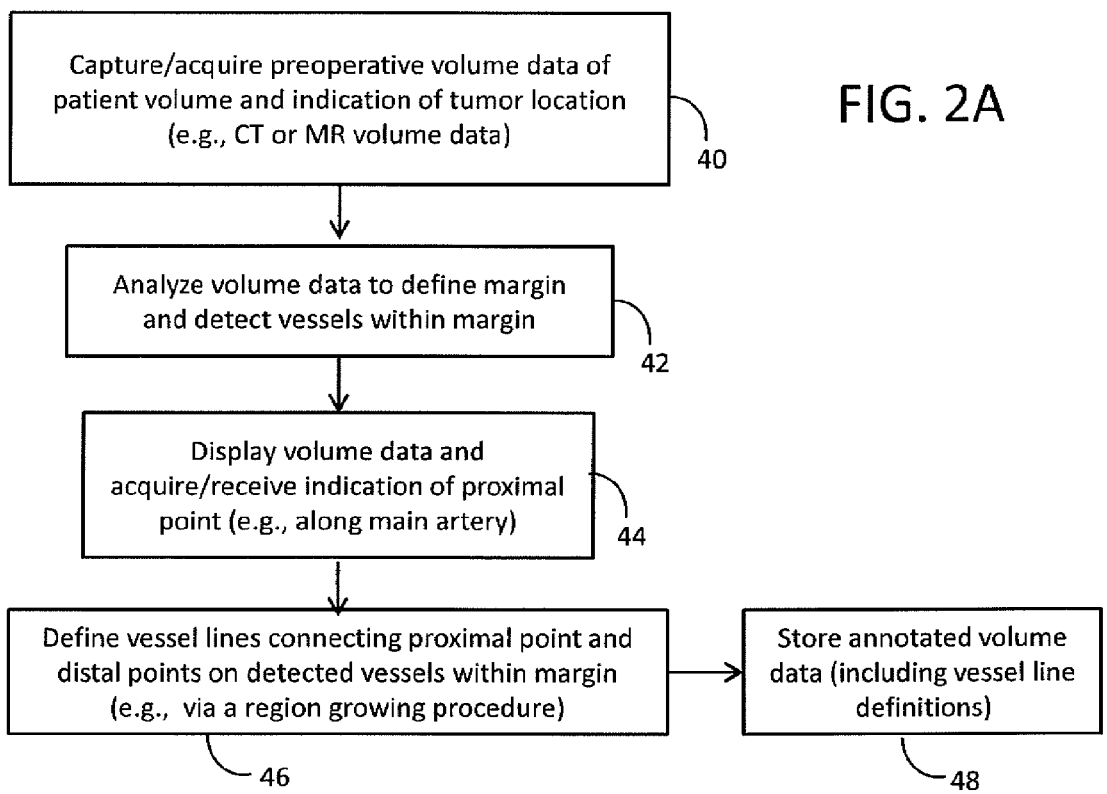
FIGS. 2A and 2B are flow chart diagrams of one embodiment of a method for displaying a catheter position relative to a patient volume during an embolization operation based on pre-operative volume data.
Figure 2B:
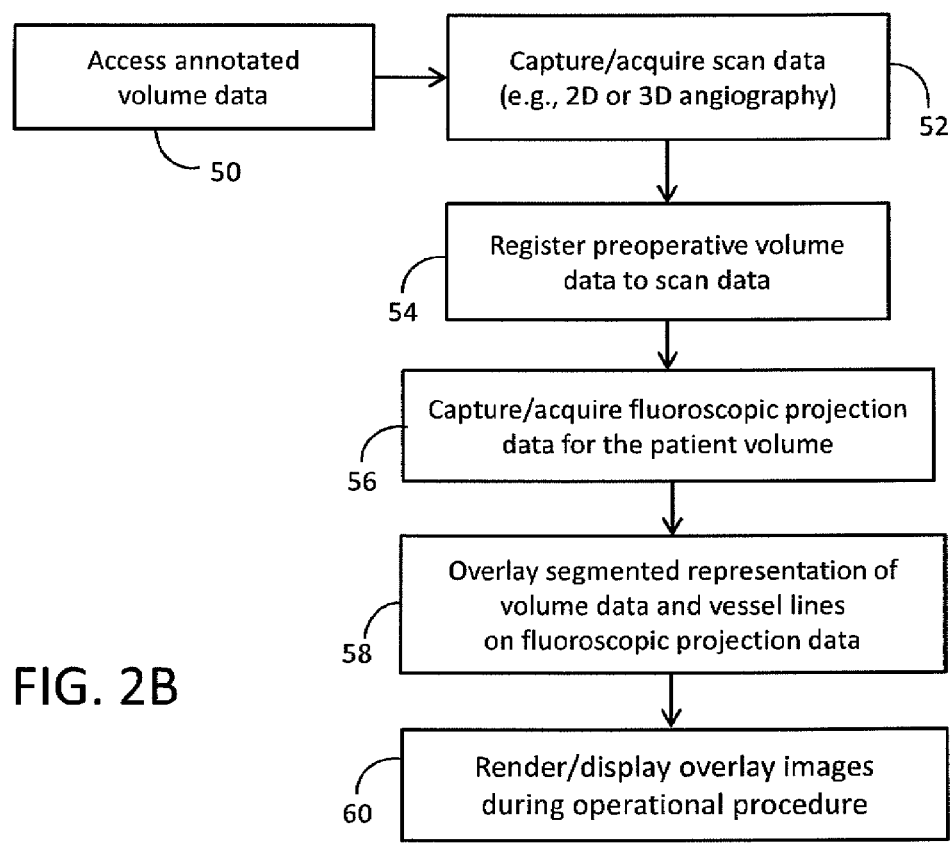

FIGS. 2A and 2B depict an embodiment of the disclosed methods in which the volume data is acquired by a scanner outside of the angiography suite in which the intervention is executed. FIG. 2A depicts a number of pre-operative imaging or scanning-related acts that are implemented. These acts may be implemented before initiation of the embolization procedure. The acts may thus be implemented in a location remote from the angiography suite. For example, the acts in FIG. 2A may be implemented during a planning, diagnosis, or other preliminary session. The acts in FIG. 2A may alternatively be implemented as, and/or nonetheless considered to be, part of the embolization procedure. FIG. 2B depicts a number of imaging or scanning-related acts that may be implemented during, or as a part of, the embolization procedure. The acts of FIG. 2B may be implemented in real time while the embolization procedure is executed.

With reference to FIG. 2A, preoperative volume data of a patient volume is acquired or captured in act 40. The volume data may be acquired via a variety of different types of imaging systems, including, for instance, a CT scanner or an MR imaging system. The volume data is segmented or otherwise processed as described above to generate an indication of the location of the BPH tumor or lesion. Such segmentation or other processing may be implemented before, during, or in connection with further analysis of the volume data in act 42 to define a margin around the lesion and detect the feeding vessels within the margin. The analysis may include the same or similar procedures to those described above.

In act 44, a representation of the volume data is rendered or displayed to allow a physician or other user to specify the location of a main or primary artery for the lesion. The user may be prompted to provide a marker or other indication. The indication is acquired or received and used as the proximal point for the vessel connection path. The path connecting the proximal point with a distal point inside the margin on a respective one of the feeding vessels is then defined or determined in act 46 as described above.

An annotated representation of the volume data may be stored in act 48. The annotated volume data may include data representative of each vessel connection path and the segmented lesion. Alternatively or additionally, data representative of the vessel connection paths and/or the segmented lesion may be stored separately from the volume data. Such data may be stored in any database or other data repository or memory (or number of such repositories or memories), whether distributed or centralized, and whether local or remote to either the preoperative scanner or the scanner used during the intervention.

With reference now to FIG. 2B, the annotated volume data is accessed in act 50 for use during the intervention. The data access procedure may involve a data transfer or other communication(s) with the data repository or memory in which such data is originally stored. The annotated volume data may thus be made available to a processor or processing system in communication or association with the equipment in the angiography suite. The data transfer or communications may occur before, during, or after implementation of one or more of the other acts of the method shown in FIG. 2B.

In act 52, scan data indicative of the patient volume is acquired, captured, and/or received. The scan data is acquired via the scanning equipment available in the angiography suite. For example, the scan data may be captured by a C-arm X-ray scanner (e.g., the above-referenced DynaCT scanner) or other rotational X-ray system. The scan data may be representative of 2D slices or 3D data. The scan data may thus be reconstructed from any number of scans of the patient volume.

A registration procedure is implemented in act 54 to transform the volume data to the coordinate system of the acquired scan data. The registration allows the vessel connection paths to be defined in the coordinate system of the scan data. The registration may include any one or more types of transformation, including, for instance, scaling, rotation, translation, warping, or combinations thereof. Any one or more image registration procedures may be used to fuse the volume data and the scan data. The scan data may be reconstructed from multiple 2D slices to support the registration process. The scan data for the 2D slices may be obtained with a low dose of contrast agent.

Once the preoperative volume data is transformed or fused to the geometry of the scan data, then any further data acquired or captured during the intervention may be rendered with an overlay as described above. In the example of FIG. 2B, fluoroscopic projection data is captured in act 56 for the patient volume. The segmented representation of the lesion in the volume data and the vessel connection paths may be overlaid on the fluoroscopic projection data in act 58. Rendering of the resulting overlay images may then occur in act 60 to support the real-time display of the overlay images during the intervention.

The order in which the acts of FIGS. 2A and 2B are implemented may vary from the example shown. For example, the volume data may be acquired for registration after the acquisition of the scan data. Some of the acts may be implemented in parallel or otherwise contemporaneously with one or more other acts.

Figure 3:
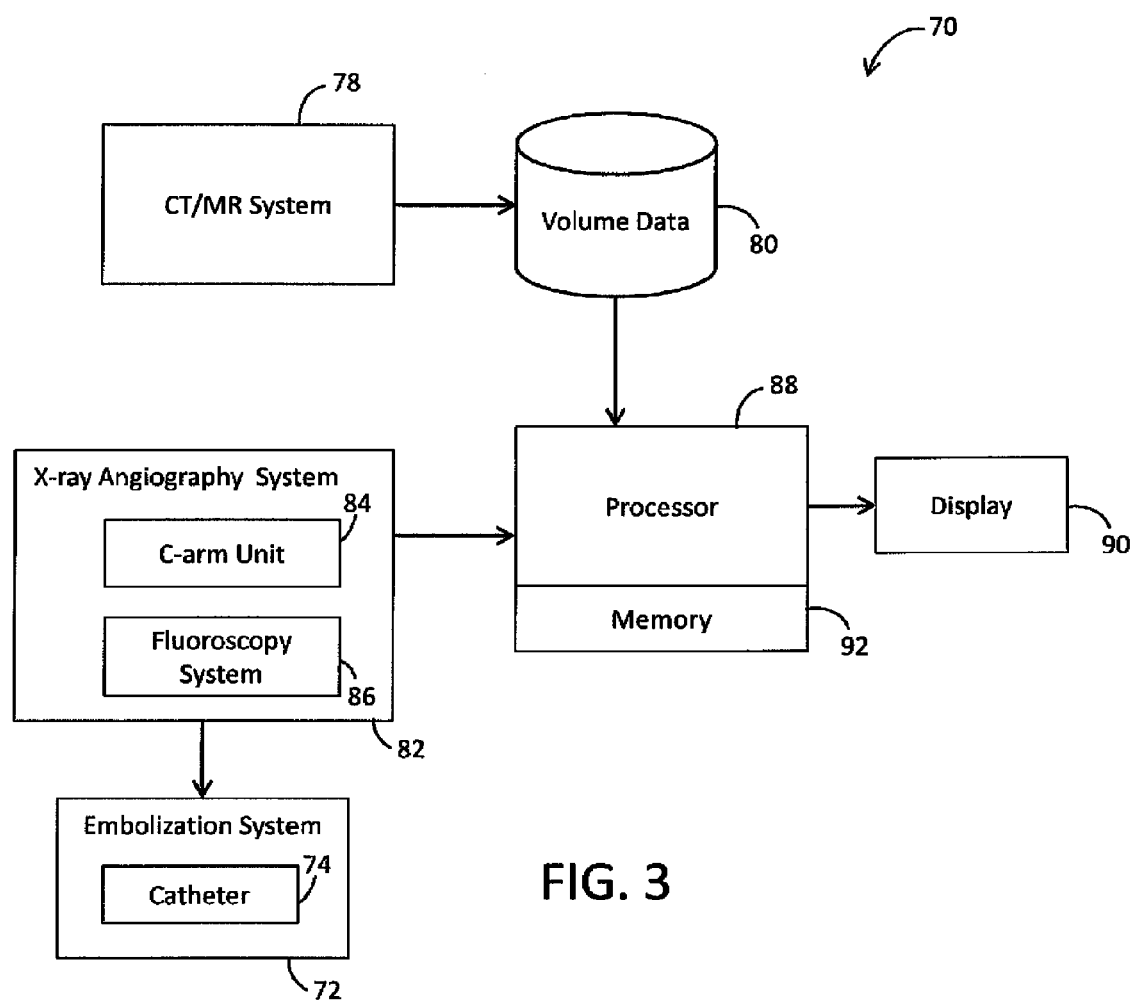
FIG. 3 is a block diagram of one embodiment of a system for displaying a catheter position relative to a patient volume during an embolization operation.

FIG. 3 depicts an exemplary system 70 configured to facilitate the implementation of an embolization operation, such as a PAE procedure. In this example, the system 70 includes an embolization system 52 configured for use in a PAE procedure for treatment of BPH. The embolization system 72 includes a catheter 74, the guidance and positioning of which may be facilitated by other components of the system 70. The system 70 may be applied to a variety of embolization treatment procedures. The system 70 need not include the catheter devices or other instruments guided during operation of the system 70. The system 70 may be adapted such that operation of one or more components of the system 70 implements one or more of the acts of the above-described methods.

The system 70 includes a CT or MR imaging system 78 to generate preliminary volume data of a patient volume. The volume data may have a high resolution. The imaging system 78 may include, for example, an x-ray imaging system and one or more processors to reconstruct the volume data from a number of x-ray scans. The imaging system 58 may instead be a multi-modal imaging system. One or more of a variety of different scanners may be used. The imaging system 78 may include one or more imaging modalities or scanners. In some embodiments, the imaging system 78 includes a PET scanner or a SPECT scanner.

The preliminary volume data is stored in a memory or other data repository 80 for later use during the treatment procedure. In this example, the data repository 80 includes a database. The configuration of the data repository 80 may vary. The data repository 80 may include any number of memories or data stores.

The imaging system 78 and the data repository 80 may be disposed remotely from one or more other components of the system 70. The imaging system 78 need not be located at the site of the embolization procedure. For example, the imaging system 78 may be located at a site at which diagnostic or planning information is captured for the patient. The imaging system 78 may also be remotely located from the data repository 80. The imaging system 78 may be communicatively coupled or connected with the data repository 80 and one or more other components of the system 70 via any communication technology, such as a network.

The system 70 further includes an x-ray imaging system 82 operable to generate intra-treatment scan data of the patient volume and to generate fluoroscopic projection data for the patient volume. The x-ray imaging system may thus be located in an angiography suite. The x-ray imaging system 82 may include a C-arm unit 84 to generate the intra-treatment scan data, and a fluoroscopy system 86 to generate the fluoroscopic projection data. These and other components of the x-ray imaging system 82 may be integrated to any desired extent. The C-arm unit 84 may include a C-shaped structure having ends on which an x-ray source and a detector are mounted. The patient volume is disposed between the ends of the C-shaped structure. In one example, the C-arm unit 84 is the Zxiom Artis dTA DynaCT system commercially available from Siemens AG (Erlangen, Germany).

The C-arm unit 84 may be configured to implement 3D rotation scans. For example, the C-shaped structure may be mounted to permit rotational movement about two axes for spherical motion. The C-arm unit 84 may thus be configured to generate 3D scan data of the patient volume. Alternatively or additionally, the C-arm unit 84 may be configured to implement multiple slice scans of the patient volume such that the scan data includes 2D scan data. The 2D or 3D scan data may be directed to any portion of the patient volume for which the preliminary volume data is acquired. The patient volumes scanned by the imaging system 78 and the X-ray system 82 may overlap to any desired extent.

The fluoroscopy system 86 may be configured to provide fluoroscopic projection data in real-time during the treatment procedure. The fluoroscopy system 86 may include a fluorescent screen, an image intensifier, and an image sensor, such as a charge coupled device (CCD) (e.g., a CCD video camera), to generate the fluoroscopic projection data. One or more components of the image intensifier may be provided by the C-arm unit 84. For example, the x-ray source of the C-arm unit 84 is used as the source for the fluoroscopy system 86. The fluoroscopic projection data may be configured for display of real-time moving images. Such images may be used during one or more parts of the embolization procedure. During other parts of the embolization procedure, the preliminary volume data is fused with the fluoroscopic projection data to support a 3D view or rendering of the lesion, the vessel connection paths, and the catheter 74 (and any other instruments or treatment devices in the patient volume).

The catheter 74 is any now known or later developed catheter for intervention or other use within a patient. The catheter 74 is sized and shaped for use in the circulatory system, such as having a diameter of 10 French or less, but a length of a foot or more. The catheter 74 is adapted for insertion within the patient, such as through a vessel or vein for extending into a heart chamber. The catheter 74 may include guide wires or be inserted through another previously positioned housing or catheter. The catheter 74 may include an electrode, scalpel, balloon, stent, portal, or channel, or other device for use during the embolization procedure.

The system 70 also includes a processor 88 in communication with one or more of the above-described components of the system 70 to process the data generated thereby and present the processed data via a display 90. For instance, the processor 88 may be configured to transform or otherwise process the preliminary volume data as described above. The processor 88 may access the data repository 80 or otherwise receive the preliminary volume data provided by the imaging system 78. The processor 88 may be configured to implement one or more image registration procedures to transform or align the preliminary volume data with the intra-treatment scan data provided by the x-ray system 82. Once the volume data is registered to the coordinate system of the intra-treatment scan data, the processor 88 may then generate a representation of the fluoroscopic projection data with the above-described overlay. The display 90 is then operable to display the representation during the embolization procedure as described above.

The intra-treatment scan data and the fluoroscopic projection data may be obtained from the x-ray system 82 via any communication technology. Alternatively or additionally, the processor 88 may be integrated with the x-ray system 82 to implement one or more processing tasks of the x-ray system 82 involved in the generation of such data.

The processor 88 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for determining position and/or generating images. The processor 88 is a single device or multiple devices operating in serial, parallel, or separately. The processor 88 may be a main processor of a computer, such as a laptop or desktop computer, or may be a processor for handling some tasks in a larger system, such as in an imaging system.

The system 70 may include a memory 92 in communication with the processor 88. The memory 92 may store data representative of the above-described preoperative and intra-treatment data, as well as fluoroscopic data, in one or more stages of processing. The memory 92 is a graphics processing memory, a video random access memory, a random access memory, system memory, random access memory, cache memory, hard drive, optical media, magnetic media, flash drive, buffer, database, combinations thereof, or other now known or later developed memory device for storing data or video information. The memory 92 is part of an imaging system, part of a computer associated with the processor 88, part of a database, part of another system, or a standalone device. The memory 92 may store one or more datasets representing the patient volume.

The acts described in connection with FIGS. 1, 2A, and 2B may be implemented via instructions executed by the programmed processor 88 for guiding the embolization operation. Data representative of the instructions may be stored in the memory 92. The acts may be implemented by one or more processors and one or more memories in addition or alternative to the processor 88 and the memory 92. The instructions may include computer code to direct the processor 88 or other processor(s) to perform the acts described above. Additional, fewer, or different operations or acts may be implemented. For example, the pre-operative data may already be stored and accessible to the processor 88 or other processor(s).

The memory 92 or other memory is a non-transitory computer readable storage medium storing data representing instructions executable by the programmed processor 88 for guiding a catheter during an embolization procedure. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

Additional, fewer, or different components may be provided. For example, the imaging system 78 may not be used in embodiments in which the x-ray angiography system 82 generates the volume data. A network or network connection may be provided, such as for networking with a medical imaging network or data archival system. One or more user inputs or other user interfaces may be provided. In another embodiment, the system 70 includes one or more components directed to validating the success of the embolization procedure. Color Doppler flow data may be acquired both before and after the embolization procedure by an ultrasound system to confirm a reduction in, or elimination of, blood flow to the lesion. Alternatively or additionally, further volumetric imaging of the patient volume may be conducted by the imaging system 78 or another imaging system after the intervention to confirm that the lesion volume has decreased.

The methods, systems, and computer readable media described above may help embolization procedures achieve positive clinical outcomes due to the selective guidance provided by the vessel connection paths. Such guidance is provided via an overlay of vessel connection paths data on real-time (e.g., fluoroscopic) images generated during an embolization procedure. The resulting images with overlays may then be used by the physician for guiding a catheter during the embolization operation.

The vessel connection paths are defined and displayed in an automated manner as described above. Such automation may reduce the time expended by the physician during the operation. The physician need not investigate the volume data to determine the correct path for the catheter. A correct path may be identified before advancing the catheter. Incorrect paths, and the time wasted on such paths, may be avoided. With these decreases in operation time, the amount of contrast agent may thus be reduced.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method of guiding a catheter during an embolization operation for a lesion, the method comprising:
   receiving volume data of a patient volume, the patient volume including the lesion and a feeding vessel for the lesion;
   defining, with a processor, a margin around the lesion in the volume data, wherein defining the margin comprises determining, with the processor, a margin boundary extended outward a distance from a boundary of the lesion;
   detecting, with the processor, the feeding vessel in the volume data;
   defining, with the processor, a vessel connection path for the feeding vessel, the vessel connection path connecting first and second points in the volume data, the second point being disposed along the feeding vessel within the margin boundary;
   receiving, via an x-ray imaging system, fluoroscopic projection data of the patient volume and the catheter, the fluoroscopic projection data being generated by the x-ray imaging system; and
   displaying, on a display device, an image of the patient volume and the catheter via the fluoroscopic projection data with an overlay during the embolization operation, the overlay comprising the vessel connection path for the feeding vessel;
   wherein detecting the feeding vessel comprises detecting, with the processor, the second point via analysis of the volume data.

2. The method of claim 1, further comprising detecting a position of a catheter tip in the volume data, wherein the first point in the volume data is the position of the catheter tip.

3. The method of claim 1, further comprising:
   displaying a representation of the volume data; and
   receiving a user specification of a position in the displayed representation indicative of a point along an artery for the feeding vessel, wherein the first point in the volume data corresponds with the position of the received user specification.

4. The method of claim 1 wherein detecting the feeding vessel comprises implementing a segmentation procedure to define a representation of the lesion in the volume data.

5. The method of claim 1 wherein detecting the feeding vessel further comprises:
   generating a histogram analysis of the volume data; and
   detecting the feeding vessel in the volume data based on the histogram analysis.

6. The method of claim 5, wherein defining the margin comprises implementing a segmentation procedure to define a representation of the lesion in the volume data, and wherein detecting the feeding vessel is implemented on a pre-segmentation representation of the volume data.

7. The method of claim 5 wherein defining the vessel connection path comprises implementing a region growing procedure.

8. The method of claim 1, further comprising:
   acquiring scan data of the patient volume during the embolization operation; and
   registering the received volume data to a coordinate system of the acquired scan data.

9. The method of claim 1, wherein:
   detecting the feeding vessel comprises detecting the feeding vessel within the margin of the lesion; and
   the margin is defined based on the boundary of the lesion and a diameter of the lesion such that the distance is determined in a relative manner based on the diameter of the lesion.

10. The method of claim 1, wherein:
    defining the margin comprises implementing a segmentation procedure to define a segmented representation of the lesion in the volume data;
    the margin is defined based on results of the segmentation procedure; and
    the overlay further comprises the segmented representation of the lesion.

11. A non-transitory computer readable storage medium having stored therein data representing instructions executable by a programmed processor for guiding a catheter during an embolization operation for a lesion, the instructions comprising computer code to:
    receive volume data of a patient volume, the patient volume including the lesion and a feeding vessel for the lesion;
    determine a margin boundary extended outward a distance from a boundary of the lesion to define a margin around the lesion in the volume data;
    detect the feeding vessel in the volume data;
    define a vessel connection path for the feeding vessel, the vessel connection path connecting first and second points in the volume data, the first point being disposed along an artery for the feeding vessel and the second point being disposed along the feeding vessel within the margin boundary;

receive, via an x-ray imaging system, fluoroscopic projection data of the patient volume and the catheter, the fluoroscopic projection data being generated by the x-ray imaging system; and render an image from the fluoroscopic projection data of the patient volume and the catheter during the embolization operation, the image additionally comprising the vessel connection paths for the feeding vessel;

wherein the computer code to detect the feeding vessel is configured to detect the second point via analysis of the volume data.

12. The computer readable storage medium of claim 11, the instructions comprising further computer code to detect a position of a catheter tip in the volume data, wherein the first point in the volume data is the position of the catheter tip.

13. The computer readable storage medium of claim 11, the instructions comprising further computer code to:

display a representation of the volume data; and receive a user specification of a position in the displayed representation indicative of a point along an artery for the feeding vessel, wherein the first point in the volume data corresponds with the position of the received user specification.

14. The computer readable storage medium of claim 11 wherein the instructions to detect the feeding vessel are configured to:

generate a histogram analysis of the volume data; and detect the feeding vessel in the volume data based on the histogram analysis.

15. The computer readable storage medium of claim 14, wherein the instructions to define the margin comprises further computer code to implement a segmentation procedure to define a representation of the lesion in the volume data, and wherein the instructions to detect the feeding vessel are implemented on a pre-segmentation representation of the volume data.

16. The computer readable storage medium of claim 14 wherein the instructions to define the vessel connection path comprises implementing a region growing procedure.

17. The computer readable storage medium of claim 11, the instructions comprising further computer code to:

receive scan data of the patient volume during the embolization operation; and register the received volume data to a coordinate system of the acquired scan data.

18. The computer readable storage medium of claim 11, wherein the margin around the lesion is defined based on a segmentation of the volume data, and wherein the margin along the feeding vessel is defined based on the boundary of the lesion and a diameter of the lesion such that the distance is determined in a relative manner based on the diameter of the lesion.

19. A system for guiding a catheter during an embolization operation for a lesion, the system comprising:

a memory in which volume data of a patient volume is stored;

an x-ray imaging system operable to generate fluoroscopic projection data for the patient volume and the catheter;

a processor configured to define a vessel connection path for a feeding vessel for the lesion and to render a representation of the patient volume and the catheter via the fluoroscopic projection data, the representation comprising the vessel connection path; and a display operable to display the representation during the embolization operation;

wherein the processor is further configured to determine a margin boundary extended outward a distance from a boundary of the lesion to define a margin around the lesion in the volume data, and to detect the feeding vessel in the volume data, the vessel connection path connecting first and second points in the volume data, the first point being disposed along an artery for the feeding vessel and the second point being disposed along the feeding vessel within the margin boundary;

wherein the processor is configured to detect the second point in the volume data via analysis of the volume data.

20. The system of claim 19, wherein the x-ray imaging system comprises a C-arm unit.

21. The system of claim 19, wherein the x-ray imaging system is configured to implement three-dimensional rotation scans and to generate the volume data.

22. The system of claim 19, further comprising a computed tomography (CT) imaging system or a magnetic resonance (MR) imaging system, the CT or MR imaging system being operable to generate the volume data.

23. The system of claim 22, wherein:

the x-ray imaging system is configured to generate scan data of the patient volume; and the processor is configured to register the volume data to a coordinate system of the scan data.

24. The system of claim 19, wherein:

the processor is configured to detect the feeding vessel within the margin of the lesion; and the margin is based on the boundary of the lesion and a diameter of the lesion such that the distance is determined in a relative manner based on the diameter of the lesion.

* * * * *